(12) United States Patent
Sumetsky

(10) Patent No.: US 7,218,803 B1
(45) Date of Patent: May 15, 2007

(54) MICROSPHERE PROBE FOR OPTICAL SURFACE MICROSCOPY AND METHOD OF USING THE SAME

(75) Inventor: Mikhail Sumetsky, Bridgewater, NJ (US)

(73) Assignee: Fitel USA Corp., Norcross, GA (US)

( * ) Notice: Subject to any disclaimer, the term of this patent is extended or adjusted under 35 U.S.C. 154(b) by 0 days.

(21) Appl. No.: 11/388,302

(22) Filed: Mar. 24, 2006

(51) Int. Cl.
    *G02B 6/00* (2006.01)
(52) U.S. Cl. .................. 385/12; 250/201.3; 250/306
(58) Field of Classification Search .............. 385/12, 385/13, 32; 250/201.3, 306, 307, 309, 216, 250/227.11; 356/436; 372/94
    See application file for complete search history.

(56) References Cited

U.S. PATENT DOCUMENTS

| | | | |
|---|---|---|---|
| 6,046,972 | A | 4/2000 | Kuroda et al. |
| 6,469,288 | B1 | 10/2002 | Sasaki et al. |
| 6,490,039 | B2 | 12/2002 | Maleki et al. |
| 6,583,399 | B1 | 6/2003 | Hunziker et al. |
| 6,744,030 | B2 | 6/2004 | Mitsuoka et al. |
| 6,795,481 | B2 | 9/2004 | Maleki et al. |
| 6,922,497 | B1 | 7/2005 | Savchenkov et al. |
| 6,995,367 | B2 | 2/2006 | Miyamoto | |
| 2004/0196465 | A1* | 10/2004 | Arnold et al. .............. 356/432 |
| 2004/0238744 | A1 | 12/2004 | Arnold et al. |
| 2006/0062508 | A1* | 3/2006 | Guo et al. ..................... 385/12 |
| 2006/0239606 | A1* | 10/2006 | Stecker ........................ 385/14 |

OTHER PUBLICATIONS

A.Mazzei, S. Gotzinger, L.de S.Menezes, V. Sandoghdar, O. Benson "Optimization of Prism Coupling to High-Q Modes in a Microsphere Resonator Using a Near-field Probe" Optics Communication 250 (2005) pp. 428-433.
M. Sumetsky, Y. Dulashko, D.J. Digiovanni, "Optical Surface Microscopy with a Moving Microsphere" Optical Society of America, 2006.
S. Gotzinger, O. Benson, V. Sandoghdar, "Influence of a Sharp Fiber Tip on High-Q Modes of a Microsphere Resonator", Optics letters, vol. 27, No. 2, Jan. 15, 2002.

* cited by examiner

Primary Examiner—Hemang Sanghavi
(74) Attorney, Agent, or Firm—Wendy W. Koba

(57) ABSTRACT

An apparatus and method for performing surface microscopy of an optical device uses an optical fiber taper including a microsphere endpoint as a near field probe. A transmission fiber is disposed adjacent to the microsphere so as to evanescently couple an optical test signal into the microsphere. A series of extremely narrow whispering gallery mode (WGM) resonances are created within the microsphere, with an associated electromagnetic field radiating outward therefrom. The microsphere probe may then be moved over the surface of an optical device being analyzed (or the device translated underneath the microsphere), where any abnormalities in the surface (such as defects, scratches and the like) will perturb the electromagnetic field pattern and be reflected in changes in the measured output power from the microsphere.

16 Claims, 5 Drawing Sheets

MICROSPHERE PROBE FOR OPTICAL SURFACE MICROSCOPY AND METHOD OF USING THE SAME

TECHNICAL FIELD

The present invention relates to a microsphere probe that may be translated across a surface to perform optical surface microscopy and, more particularly, to an optical microsphere resonator probe that performs local surface sensing with whispering gallery mode resonances.

BACKGROUND OF THE INVENTION

Whispering gallery modes (WGMs) in optical applications is typically associated with circular-path resonant cavities where light inserted into an optical WGM travels exclusively via total internal reflection, glancing off material interfaces at a near-parallel angle. In recent years, interest in WGM optical resonators has grown dramatically, particularly with respect to its "sensing" applications. Optical sensing generally uses an optical probe beam to interact with a material to be detected. This interaction between the optical probe beam and the material modifies some aspect of the optical probe beam. A portion of this modified beam, such as the scattered light, may be collected and measured to obtain certain information associated with the material. For example, the optical intensity, phase, spectrum, polarization and/or direction of the collected light may be measured either individually or in combination with other parameters to determine the composition of the material.

Recently, the optical probe for such applications has taken on the form of a microsphere formed at the termination of an optical fiber taper. Such a microsphere can possess extremely high quality (O) factor WGMs, corresponding to narrow spectral resonances. The position and width of these resonances are extremely sensitive to changes in the ambient medium. Therefore, when used as a "sensor", a microsphere probe may be immersed into the medium under test to determine its composition with extreme precision. U.S. Pat. No. 6,490,039 issued to L. Maleki et al. on Dec. 3, 2002, entitled Optical Sensing Based on Whispering-Gallery-Mode Microcavity, is exemplary of one such sensing arrangement that utilizes a microsphere cavity "whispering gallery mode" resonator to detect a minute amount of a particular material in a given specimen. U.S. Pat. No. 6,922,497 issued to A. Savchenkov et al. on Jul. 26, 2005, entitled Whispering Gallery Mode Resonators Based on Radiation-Sensitive Materials, discloses an alternative arrangement, using a pair of WGM optical resonators that are disposed in a cascaded configuration to allow for "tuning" of the sensing function.

A study of the prior art, however, yields the result that the use of a microsphere resonant probe has been limited to performing compositional analysis of a "medium under test".

SUMMARY OF THE INVENTION

The present invention is associated with expanding the utility of a microsphere resonant probe to the field of optical surface measurements (i.e., optical surface microscopy) wherein a microsphere probe is translated across the surface of an optical device (for example, a grating structure) and the WGM resonances used to provide topological information associated with the optical device.

In accordance with the present invention, a microsphere resonator is used as a near field probe which is extremely sensitive to the smallest changes in the optical properties of the "surface under test" (SUT). The sensitivity of the inventive microsphere resonator probe is provided in accordance with the extremely narrow line widths of the WGM resonances, as well as the resonant enhancement of the associated electromagnetic field (which can be very large inside the microsphere probe) and evanescently present in the immediate vicinity of the microsphere probe.

In a preferred embodiment of the present invention, the microsphere probe's performance is enhanced by including a metallic defect on the microsphere surface so as to increase the strength of the associated electromagnetic field at that location and improve the sensitivity of the measured power.

Other and further embodiments of the present invention will become apparent during the course of the following discussion and by reference to the accompanying drawings.

BRIEF DESCRIPTION OF THE DRAWINGS

Referring now to the drawings, where like numerals represent like parts in several views:

FIG. 5($c$) illustrates the use of an imbedded metal nanoparticle within the surface of the microsphere itself.

DETAILED DESCRIPTION

Figure 1:
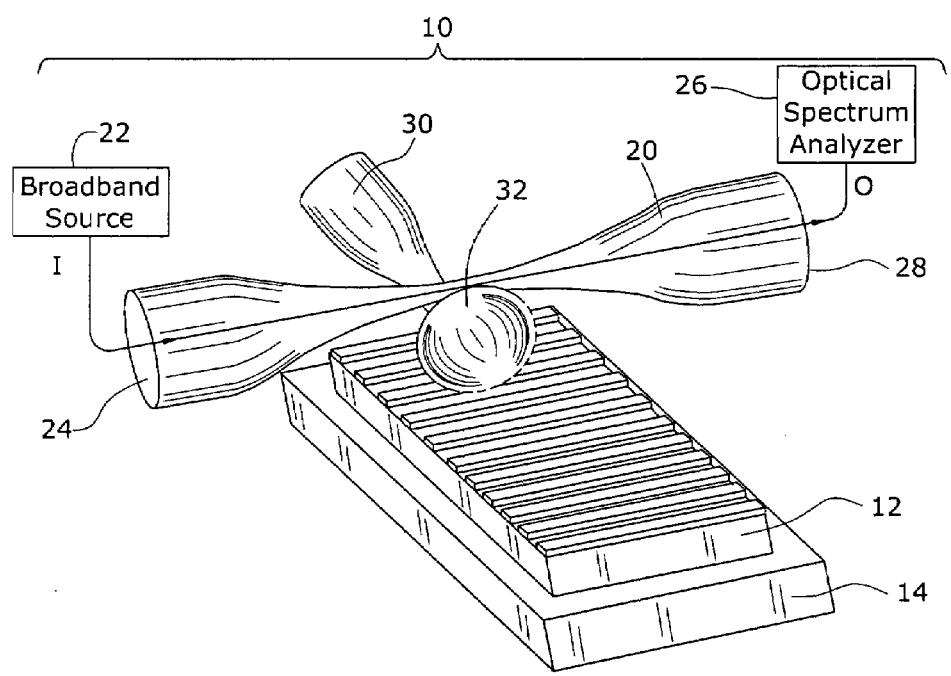
FIG. 1 illustrates an exemplary arrangement for utilizing the microsphere resonant probe of the present invention to perform optical surface microscopy.

FIG. 1 illustrates an exemplary microsphere resonant probe 10 formed in accordance with the present invention, as used in this case to assess the surface qualities of an optical phase mask 12. It is to be understood that the use of a phase mask as a "surface under test" is exemplary only; the microsphere resonant probe of the present invention may be used to investigate the surface qualities (i.e., perform optical spectroscopy) of virtually any optical device. In the particular arrangement as illustrated in FIG. 1, optical phase mask 12 is placed upon a translation table 14 which moves in the direction shown to allow for microsphere resonant probe 10 to scan the entire surface of mask 12.

In accordance with the present invention, microsphere resonant probe 10 comprises a light source for illuminating the surface area, in this particular case using a biconically tapered optical fiber 20, with a broadband light source 22 coupled into a first (input) end 24 of optical fiber taper 20 and an optical spectrum analyzer (OSA) 26 coupled to a second (output) end 28 of optical fiber taper 20. Various other light guiding arrangements (such as, for example, optical waveguides or free space optical transmission systems) may be used to evanescently couple the optical test signal into probe 10. OSA 26 is utilized in accordance with the present invention to monitor and collect spectral information associated with the surface under test. In particular, the results obtained by OSA 26 yield changes in resonance (aperiodic features) that can be attributed to defects or other problems with the optical surface.

Probe 10 further comprises an optical fiber taper 30, with a microsphere 32 formed at the termination thereof. The optical signal propagating along tapered optical fiber 20 will be evanescently coupled into microsphere 32 so as to create a number of WGM resonances within microsphere 32.

Figure 2:
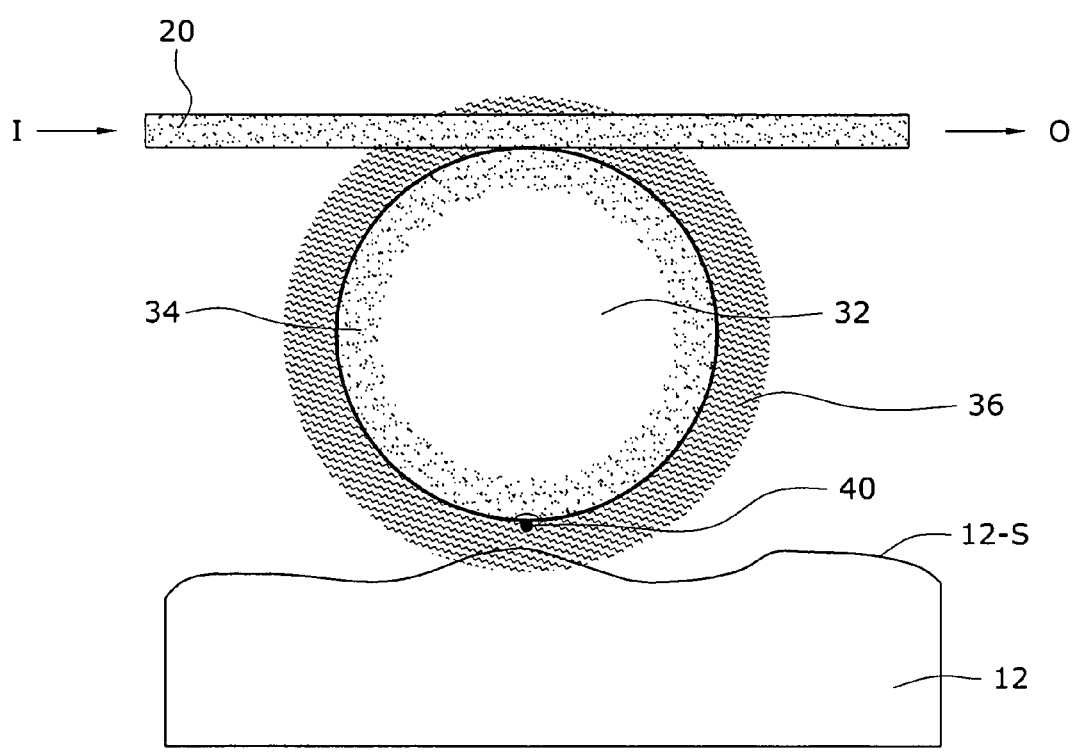
FIG. 2 is an enlarged view of the end portion of the inventive microsphere probe, illustrating in particular the relationship between the microsphere, light-supply guide (fiber) and an "optical surface under test"

FIG. 2 illustrates, in an enlarged view, a portion of the arrangement of FIG. 1, clearly illustrating in this view the relationship between microsphere 32, tapered optical fiber 20 and device 12. As mentioned above, an input optical signal passing through fiber 20 will be evanescently coupled into microsphere 32, resulting in the creation of whispering gallery modes (WGMs) within the inner surface of microsphere 32. FIG. 2 illustrates the presence of these WGMs as a darkened ring 34 for the purposes of illustration. An evanescent electromagnetic field 36 associated with WGMs 34 will radiate outward from microsphere 32 so as to penetrate surface 12-S of optical device 12. In accordance with the teachings of the present invention, any changes in surface 12-S (such as defects, scratches, etc.) will result in changing the distribution of evanescent field 36, which then changes the position of the transmission resonance as recorded by OSA 26. Thus, by observing changes in the resonance at OSA 26 (i.e., aperiodic features), the characteristics of surface 12-S may be fully observed and analyzed.

Figure 3:
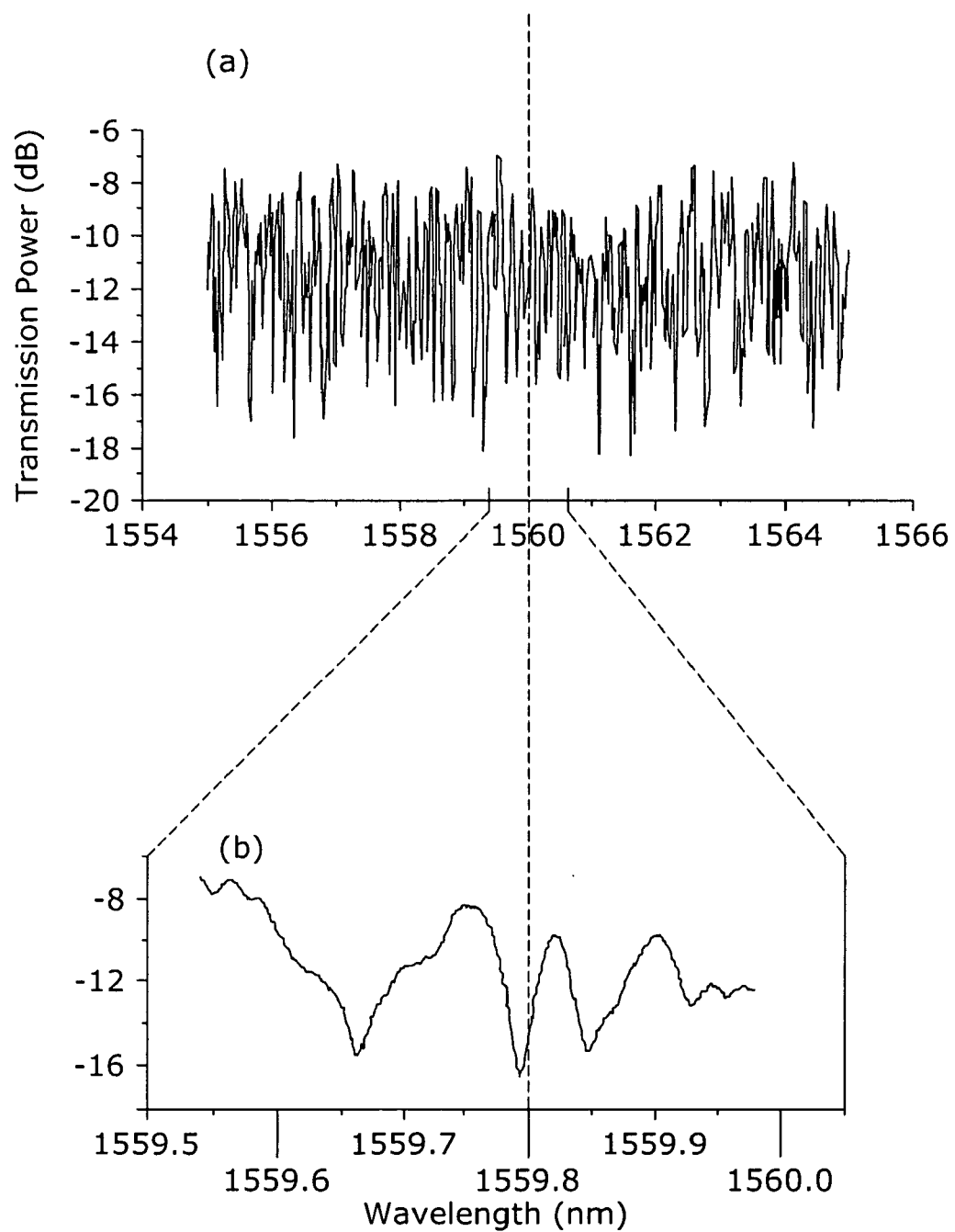
FIG. 3 illustrates an exemplary spectral response associated with the inventive microsphere when illuminated and placed over an optical surface, where FIG. 3($a$) illustrates the spectral response over a wavelength range of approximately 1555 to 1565 nm, with FIG. 3($b$) showing an expanded view of the spectrum in the vicinity a single resonance at 1559.8 nm.

FIG. 3 illustrates an exemplary transmission spectrum recorded by OSA 26 when used with microsphere resonant probe 10 of the present invention as shown in FIGS. 1 and 2. For this particular result, biconical tapered optical fiber 20 was formed to exhibit a beam waist of 1.2 μm at the point where it contacts microsphere 32. Microsphere 32 was formed to have a radius of 66 μm. Optical phase mask 12 had a grating period Λ=0.97 μm, with a grating depth of 0.26 μm and a 50% duty cycle. A broadband source was then applied to optical fiber 20 and coupled into microsphere 32, with the presence of microsphere 32 resulting in the transmission spectrum as shown in FIG. 3(*a*), where numerous resonances (WGMs) can be observed. FIG. 3(*b*) illustrates an expanded view of the spectrum in the vicinity of a single WGM, corresponding to the wavelength λ=1559.79 nm.

Figure 4:
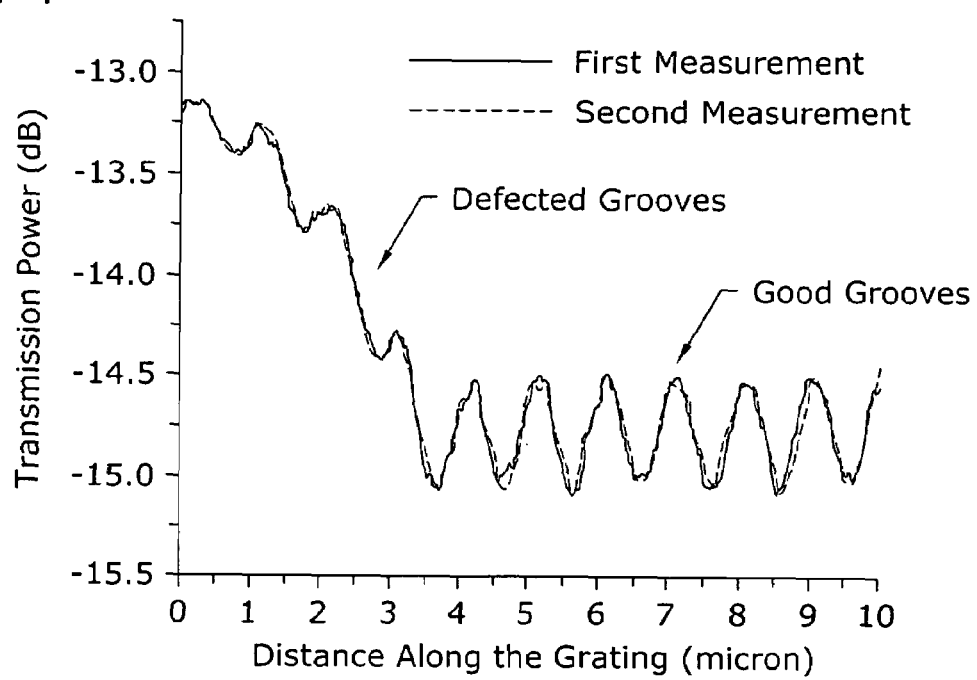
FIG. 4 is a graph of transmitted power as a function of "translated" distance along an optical device surface, measured at the resonant wavelength of 1559.8 nm.

Therefore, in accordance with the present invention, the position of device 12 with respect to probe 10 can be translated in the manner as shown in FIG. 1, with OSA 26 used to measure the transmitted optical power as a function of time at the selected wavelength of 1559.79 nm. FIG. 4 illustrates the transmission power, as recorded by OSA 26 as mask 12 was translated underneath microsphere 32. In this particular test, a mask having known defects was used, where these defects are associated with the aperiodic portion of the relationship plotted in FIG. 4.

Thus, as clearly demonstrated by the results shown in FIG. 4, a microsphere resonant probe of the present invention can be used to perform highly accurate interferometric measurements of the optical properties of a scanned surface. The resolution of the inventive microsphere resonant probe may be further enhanced by adding a nanometer-sized metallic "defect" to the microsphere at the "point of contact" with an optical device being analyzed. FIG. 2 illustrates, in general form, a defect 40 formed at tangential point T of microsphere 32. Defect 40 may have a spherical, conical or other shape (or opening in microsphere 32), as long as defect 40 provides a sharp nanometer-order diameter apex close to the surface being analyzed.

Figure 5:
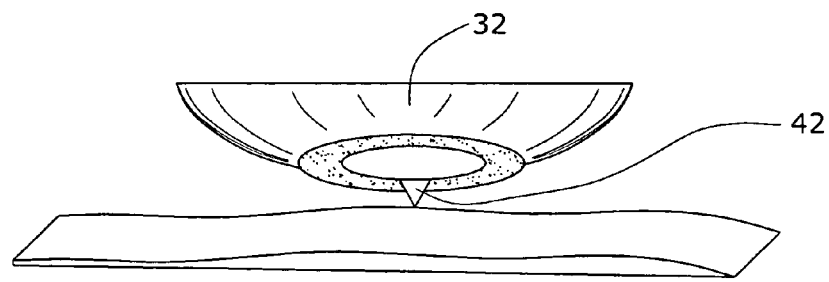
FIG. 5 illustrates three alternative microsphere embodiments useful to increase the electromagnetic field strength in the vicinity of the optical power measurement, where FIG. 5($a$) illustrates the inclusion of a metallic tip, FIG. 5($b$) illustrates the inclusion of a metallic film with a nanometer-order aperture.
Figure 5:
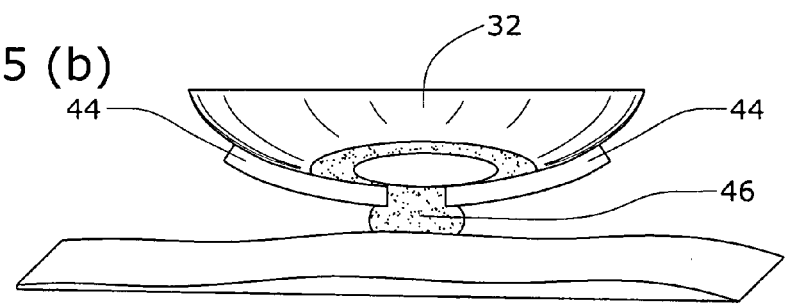
Figure 5:
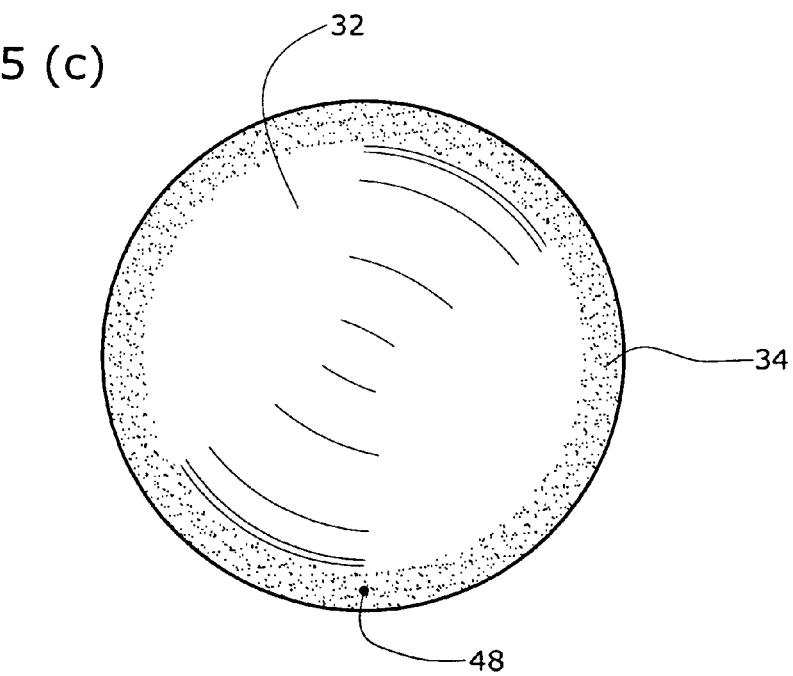

FIG. 5 illustrates three various embodiments of a metallic defect that may be used to enhance the sensitivity of the microsphere probe of the present invention. FIG. 5(*a*) shows a first embodiment, with a nanometer-sized metallic tip 42 disposed at tangential point T of microsphere 32. A metallized film 44, with a nanometer-sized aperture 46, may be formed along a portion of the bottom surface of microsphere 32, as shown in FIG. 5(*b*), may also be used to form a suitable defect for enhancing the electric field in the vicinity of the surface being analyzed. FIG. 5(*c*) illustrates yet another embodiment, in this case with a metal nanoparticle formed within the surface of microsphere 32 itself. Other embodiments are possible, the above arrangements as shown in FIG. 5 are considered to be exemplary only.

It is to be understood that the above-described embodiments of the inventive microsphere resonant probe are exemplary only; various different microsphere sizes, for example may be used, with different WGM resonant wavelengths selected for analysis. Other methods of transporting an optical signal into and out of the microsphere probe may be used as well. Thus, the present invention is intended to be limited only by the spirit and scope of the claims appended hereto.

What is claimed is:

1. An optical microsphere probe for performing surface microscopy of an optical device, the probe comprising
   an optical fiber taper including a microsphere formed at a first endpoint thereof;
   an optical signal path for supporting the transmission of an optical test signal, the optical signal path disposed with respect to the optical fiber taper so as to be in contact with the microsphere to evanescently couple the optical test signal into said microsphere and create whispering gallery mode resonances and an associated evanescent electromagnetic field therein; and
   means for measuring transmitted power exiting the optical signal path as the microsphere probe is translated over the surface of the optical device, with the electromagnetic field overlapping the optical device surface such that the transmitted power is a function of the surface morphology of said optical device.

2. An optical microsphere probe as defined in claim 1 wherein the optical signal path comprises an optical fiber disposed to contact the microsphere at a single, tangential point.

3. An optical microsphere probe as defined in claim 2 wherein the optical fiber comprises a tapered portion in the vicinity of the microsphere.

4. An optical microsphere probe as defined in claim 3 wherein the tapered optical fiber comprises a biconically tapered optical fiber.

5. An optical microsphere probe as defined in claim 4 wherein the biconically tapered optical fiber exhibits a beam waist on the order of approximately one micron.

6. An optical microsphere probe as defined in claim 1 wherein the means for measuring transmitted power comprises an optical spectrum analyzer.

7. An optical microsphere probe as defined in claim 6 wherein the optical spectrum analyzer functions to record transmitted power as the optical microsphere probe is translated along the surface of the optical device, with surface irregularities recognized as aperiodic features in the recorded power signal.

8. An optical microsphere probe as defined in claim 1 wherein the microsphere is formed to include a singular, nanometer-order defect to enhance the strength of the electromagnetic field and increase the resolution of the transmitted power measurement.

9. An optical microsphere probe as defined in claim 8 wherein the singular, nanometer-order defect comprises a nanometer-order metallic tip disposed at one point along the surface of said microsphere.

10. An optical microsphere probe as defined in claim 8 wherein the singular, nanometer-order defect comprises a metallic film disposed over a portion of the microsphere surface, the metallic film include a nanometer-order opening.

11. An optical microsphere probe as defined in claim 8 wherein the singular, nanometer-order defect comprises a nanometer-order aperture formed at a single location on the microsphere surface.

12. An optical microsphere probe as defined in claim 8 wherein the singular, nanometer-order defect comprises a metallic nanoparticle embedded within a surface portion of the microsphere.

13. A method of performing optical surface microscopy using a microsphere probe, the method comprising the steps of:
   a) illuminating a microsphere with an optical test signal to create whispering gallery modes (WGM) resonances therein, the resonances creating an electromagnetic field radiating outward therefrom;
   b) selecting a specific WGM resonant wavelength for performing microscopy and illuminating the microsphere with the selected WGM resonant wavelength;
   c) translating the microsphere across a surface of an optical device being analyzed in a manner such that the radiated electromagnetic field overlaps the device surface; and
   d) recording transmitted optical power, at the selected WGM resonant wavelength, as a function of distance along the surface, wherein the transmitted optical power is a function of the surface morphology of said optical device.

14. The method as defined in claim 13 wherein the method further comprises the step of:
   e) evaluating the recorded optical measurements for aperiodic features, aperiodic features associated with irregularities in the surface morphology of the optical device.

15. The method as defined in claim 13 wherein in performing step a), an optical fiber is used to support the transmission of the optical test signal.

16. The method as defined in claim 13 wherein in performing step a), a microsphere including a nanometer-sized defect is used, the defect resulting in increasing the strength of the radiated electromagnetic field and improving the resolution of the optical power measurement recorded in step d).

* * * * *